United States Patent

Abraham-Fuchs et al.

(12) United States Patent
(10) Patent No.: US 7,704,214 B2
(45) Date of Patent: Apr. 27, 2010

(54) DEVICE AND METHOD FOR THE QUANTITATIVE DETERMINATION OF NITROGEN OXIDES IN EXHALED AIR AND APPLICATION THEREOF

(75) Inventors: Klaus Abraham-Fuchs, Erlangen (DE); Maximilian Fleischer, Höhenkirchen (DE); Hans Meixner, Haar (DE); Eva Rumpel, Erlangen (DE); Elfriede Simon, München (DE)

(73) Assignee: Siemens Aktiengesellschaft, Munich (DE)

( * ) Notice: Subject to any disclaimer, the term of this patent is extended or adjusted under 35 U.S.C. 154(b) by 821 days.

(21) Appl. No.: 10/476,444

(22) PCT Filed: Apr. 30, 2002

(86) PCT No.: PCT/DE02/01576

§ 371 (c)(1),
(2), (4) Date: Oct. 30, 2003

(87) PCT Pub. No.: WO02/088691

PCT Pub. Date: Nov. 7, 2002

(65) Prior Publication Data

US 2004/0133116 A1    Jul. 8, 2004

(30) Foreign Application Priority Data

Apr. 30, 2001    (DE) ................ 101 21 262

(51) Int. Cl.
*A61B 5/08* (2006.01)
*G01N 31/00* (2006.01)

(52) U.S. Cl. ............... 600/532; 600/529; 73/23.3; 422/84

(58) Field of Classification Search ........... 436/117, 436/118; 422/84; 73/23.3; 600/532
See application file for complete search history.

(56) References Cited

U.S. PATENT DOCUMENTS 4,381,922 A * 5/1983 Frey et al. .............. 422/98

(Continued)

FOREIGN PATENT DOCUMENTS

DE    198 14 857 A1    10/1999

(Continued)

OTHER PUBLICATIONS

Lampe U et al.: "Nitrogen oxide sensors based on thin films of BaSn03" Sensors and Actuators B, Elsevier Sequoia S.A., Lausanne, CH, Bd. 26, Nr. 1-3,1995, Seiten 97-98, XP004318432 ISSN:0925-4005 Zusammenfassung.

(Continued)

*Primary Examiner*—Patricia C Mallari
(74) *Attorney, Agent, or Firm*—Harness, Dickey & Pierce, P.L.C.

(57) ABSTRACT

A volumetric flow of an analyte, including exhaled air, is fed to a gas sensor unit by used of gas flow device, which can include various sensors for the determination of nitrogen oxides. An oxidation catalyst is used when using an $NO_2$ sensor, which converts nitrogen monoxide to nitrogen dioxide and the gas sensor unit measures the content of nitrogen dioxide. The nitrogen monoxide content is calculated from the nitrogen dioxide content. In order to eliminate cross-sensitivity moisture and ethanol are also measured. The device can be applied to the determination of nitrogen monoxide content of exhaled air.

31 Claims, 4 Drawing Sheets

U.S. PATENT DOCUMENTS

| | | | | |
|---|---|---|---|---|
| 4,608,232 | A | * | 8/1986 | Sunano et al. .................. 422/88 |
| 4,840,913 | A | * | 6/1989 | Logothetis et al. ........... 436/116 |
| 5,045,285 | A | * | 9/1991 | Kolesar, Jr. ................... 422/98 |
| 5,411,709 | A | * | 5/1995 | Furuki et al. ................... 422/91 |
| 5,431,883 | A | * | 7/1995 | Barraud .................... 422/82.01 |
| 5,866,075 | A | * | 2/1999 | Gupta et al. ................... 422/88 |
| 6,038,913 | A | | 3/2000 | Gustafsson et al. |
| 6,111,280 | A | * | 8/2000 | Gardner et al. ............... 257/253 |
| 6,711,470 | B1 | * | 3/2004 | Hartenstein et al. .......... 700/276 |

FOREIGN PATENT DOCUMENTS

| | | |
|---|---|---|
| EP | 0 699 414 | 3/1996 |
| JP | 59091355 A * | 5/1984 |
| WO | WO 01/26547 | 4/2001 |

OTHER PUBLICATIONS

Robinson J.K. et al.: "Luminol/H2O2 Chemiluminescence Detector for the Analysis of Nitric Oxide in Exhaled Breath" Analytical Chemistry, American Chemical Society/ Columbus, US, Bd. 71, Nr. 22, Nov. 15, 1999, Seiten 5131-5136, XP000926903 ISSN: 0003-2700 Zusammenfassung.

Leu M. et al.: "Evaluation of Gas Mixtures With Different Sensitive Layers Incorporated in Hybrid Fet Structures" Sensors and Actuators B., Elsevier Sequoia S.A., Lausanne, CH, Bd. B18, 1994, Seiten 678-681, XP000861740 ISSN: 0925-4005 Absätze '002.!, '003.!; Abbildung 1; Tabelle 1.

Cantalini C. et al.: "Cross sensitivity and stability of N02 Sensors from W03 thin film" Sensors and Actutators B., Elsevier Sequoia S.A., Lausanne, CH, Bd. 35, Nr. 1, Sep. 1, 1996, Seiten 112-118, XP004049740 ISSN:0925-4005 Zusammenfassung.

Barker P.S. et al.: "A hybrid phthalocyanine /silicon field-effect transistor sensor for N02" Thin Sold Films, Elsevier-Sequoia S.A. Lausanne, CH, Bd. 284-285, Sep. 15, 1996, Seiten 94-97,XP004078110 ISSN:0040-6090 Absätze '002.!, '3. 2.!; Abbildungen 1,2.

Shu ji Qin et al.: "The Sensitivity to N02 of Sandwich Devices Based on Lead Phthalocyanine and Copper Phthalocyanine" Senors and Actuators B, Elsevier Sequoia S.A., Lausanne, CH, Bd. B3, Nr. 4, Apr. 1, 1991, Seiten 255-260, XP000243207 ISSN: 09250-4005 Zusammenfassung.

Uwe Lampe et al. "Nitrogen oxide sensors based on thin films of $BaSnO_3$." Sensors and Actuators B, Elsevier Science S.A. 26-27 (1995) pp. 97-98.

Shu Ji Qin and B. Bott. "The sensitivity to $NO_2$ of sandwich devices based on lead phthalocyanine and copper phthalocyanine." Sensors and Actuators B, Elsevier Sequoia, Lausanne 3 (1991) pp. 255-260.

P.S. Barker et al. "A hybrid phthalocyanine/silicon field-effect transistor sensor for $NO_2$." Thin Solid Films, Elsevier Science S.A. 284-285 (1996) pp. 94-97.

Cantalini et al. "Cross sensitivity and stability of $NO_2$ sensors from $WO_3$ thin film." Sensors and Actuators B, Elsevier Science S.A. 35-36 (1996) pp. 112-118.

Leu et al. "Evaluation of gas mixtures with different sensitive layers incorporated in hybrid FET structures." Sensors and Actuators B, Elsevier Sequoia 18-19 (1994) 678-681.

Robinson et al. "Luminol/$H_2O_2$ Chemiluminescence Detector for the Analysis of Nitric Oxide in Exhaled Breath." Analytical Chemistry, vol. 71, No. 22, Nov. 15, 1999, pp. 5131-5136.

* cited by examiner

- heliogen blue G, T: 113°C
- PC phenylether derivative, T: 90°C

FIG 8

- Co-protoporphyrine, T: 30°C
- Protoporphyrine Na salts, T: 47°C

DEVICE AND METHOD FOR THE QUANTITATIVE DETERMINATION OF NITROGEN OXIDES IN EXHALED AIR AND APPLICATION THEREOF

This application is the national phase under 35 U.S.C. §371 of PCT International Application No. PCT/DE02/01576 which has an International filing date of Apr. 30, 2002, which designated the United States of America and which claims priority on German Patent Application number DE 101 21 262.3 filed Apr. 30, 2001, the entire contents of which are hereby incorporated herein by reference.

FIELD OF THE INVENTION

The invention generally relates to a device and a method for the quantitative measurement of nitrogen oxides, particularly nitrogen dioxide, whereby the original content of nitrogen monoxide can be calculated. Furthermore, the invention generally relates to the application of this device in conjunction with respiratory tract diseases, such as asthma.

BACKGROUND OF THE INVENTION

Among 5% of adults and 15 to 20% of children in western industrial nations asthma is one of the most frequently-occurring diseases, and this tendency is increasing.

Inflammatory conditions of the lower respiratory tracts, such as asthma or bronchiectasis, are accompanied by an increased nitrogen monoxide (NO) concentration of up to 85 ppb in the exhaled air. A reduction in the NO concentration is observed when treated with anti-inflammatory medicines such as corticosteroids. An imminent asthma attack is clearly indicated earlier by the rise in the NO content of the exhaled air than in a pulmonary function test. Nitrogen monoxide is thus a preliminary sign of an asthma attack. Measuring this NO in the exhaled air is thus an ideal method of diagnosis, particularly for deciding treatment and checking the progress of treatment of asthma and other diseases associated with inflammation of the lower respiratory tracts.

A precondition for checking the progress of treatment is, however, a mobile cost-effective measuring instrument for the quantitative detection of nitrogen dioxides regardless of location. A constant telemedical care of chronic diseases would also be of interest.

The accuracy required for the detection of nitrogen oxide in exhaled air in conjunction with the aforementioned diseases is in the area of a few ppb NO. Up to now, this could be achieved only by way of chemo luminescence measurements. The disadvantages are on one hand the size, with a weight of at least 45 kg, and on the other the high cost of such a chemo luminescence measuring apparatus. Up to now, the use of this equipment has been limited to clinics and specialized practices.

At present, peak-flow meters are used to check the progress of, for example, asthma. These are small devices that enable a simple pulmonary function test. In contrast to the complete pulmonary function test, only the highest respiration flow level, the forced expiratory value is measured. This is created at maximum exhalation. The measurement is taken several times a day. The device is relatively inexpensive. However, it measures only the end result of an asthma attack, i.e. the narrowing of the airways, and not a preliminary sign of an attack, such as for example nitrogen monoxide would indicate. Valuable time for preventive treatment is thus lost.

Further evidence of an inflammatory condition of the lower respiratory tracts can also be gained from the bronchial mucus, the sputum. A general sputum examination is macroscopic, microscopic and bacteriological and is comparatively time consuming. Obtaining mucus from children and patients with severe breathing difficulties is either impossible or very difficult.

SUMMARY OF THE INVENTION

An object of an embodiment of the invention is to provide a simple measuring system for the quantitative measurement of nitrogen oxides that is as independent of location as possible and to provide a method of operation with the nitrogen monoxide content in the exhaled air being detectable during the care of patients with respiratory illnesses.

An embodiment of the invention involves achieving a mobile cost-effective, quantitative measurement of nitrogen oxides in exhaled air by an apparatus that has a device for guiding the volumetric flow of the exhaled air in succession to an oxidation catalyst for oxidation of the nitrogen monoxide content to nitrogen dioxide, to a gas sensor unit for detection of nitrogen dioxide, moisture and ethanol and also to a unit for calculating the nitrogen monoxide values from the nitrogen dioxide values, with the moisture and ethanol concentrations eliminating the cross-sensitivity of the nitrogen oxide measurements. The combination of a very precise nitrogen oxide measuring method, with which the quantitative measurement of nitrogen oxides in the exhaled air is also possible, with a suitable test setup that guarantees the preparation of the measured gas mixture together with the calculation of the nitrogen monoxide content in the exhaled air, provides a cost-effective gas sensor system for detection of the nitrogen monoxide content and enables conclusions to be drawn regarding respiratory illnesses.

The use of a gas sensor operating on the principle of work function measurement for the detection of nitrogen oxide has energy advantages. This enables measurements to be taken with a relatively low heat energy requirement, which makes the development of a cost-effective sensor easier. It also enables applications with sensors to be opened up that because of the environment would be required to have a low electrical power. Furthermore, the use of this measuring principle has the advantages of a relatively wide range of sensitive materials that are relatively easy to prepare. Generally, however, gas sensors can be used that can detect between 3 and 100 ppb in the target area with a sufficiently high resolution. Semi-conducting metal oxide gas sensors can also particularly be used in this case, or a sensor using the principle of work function measurement.

An advantageous embodiment of the invention provides that the volumetric flow of the exhaled air is divided in the apparatus, with a part volumetric flow being directed via the oxidation catalyst and then to the nitrogen oxide measurement and another part volumetric flow being sent directly to the nitrogen oxide measurement. In this way, verification of the nitrogen monoxide in the exhaled air can particularly be determined without disturbance from nitrogen oxide from the ambient air. The actual nitrogen monoxide content of the exhaled air can be determined without error from the difference in the nitrogen dioxide concentration. The volumetric flow is measured using conventional measuring methods.

Various field effect transistors are known for nitrogen oxide detection using the principle of work function measurement, with the gas-sensitive layer being represented as a gate electrode. This gate electrode can be separated from the channel area of the field effect transistor by an air gap. A change in the potential between the gate and channel area ($\Delta V_G$) is used as the basis for a detecting measuring signal. Hybrid flip— chip arrangements of gas sensors that are designed as CMOS transistors are known, for example, from German patent applications No. 198 14 857.7 and No. 199 56 806.5. A gas sensor can also be fitted with two field effect transistors, the control characteristic of which can be matched by approximately equal air gaps between the channel area and gate electrode and the sensor layers of which can be separately read. German patent application No. 199 56 744.1 describes how the clearance between the gate electrode and channel area of a field effect transistor can be reproducibly represented by extremely precise spacers. In a different embodiment the gas-sensitive material is applied in porous form to the channel area or gate.

Cross-sensitivities can be eliminated by combining several individual sensors in a gas sensor unit in the form of various gas-sensitive layers. One layer must of course be sensitive to the target gas. Further gas-sensitive layers are designed for the detection of moisture or alcohol. A reference layer is, for example, insensitive. The integration of different gas-sensitive layers of this kind in a gas sensor unit enables the effects of moisture and alcohol to be eliminated.

To eliminate interference with the measurement due to the effect of the difference between the exhaled air temperature or measured gas temperature and sensor temperature, it is also necessary to perform temperature compensation by using a second transistor. For the selective detection of exhaled gases it is particularly necessary to take account of the effect of moisture, because the concentration of moisture can rise up to 100% relative air humidity. Furthermore, it is also recommended that the concentration of alcohol be taken into account because this component can occur in very high concentrations in the exhaled gas compared to nitrogen oxides.

A layer combination, for example, looks as follows:

target-gas sensitive layer; gas-insensitive reference layer; moisture-sensitive layer; moisture-insensitive reference layer; alcohol-sensitive layer; alcohol-insensitive layer and temperature sensor, in one unit. This enables interference with the measurement due to the influence of deviations between the temperature of the exhaled air and the sensor operating temperature, the effects of moisture and of alcohol contained in the breath to be eliminated.

Gas-sensitive layers for use in an SG-FET (Suspended Gate Field Effect Transistor) can advantageously be porphine pigments, such as phthalocyanines with a central atom of copper or lead. At sensor temperatures between 50° and 120°, nitrogen oxide sensitivities down to the lower ppb range can be verified. Detection is, as normal, aimed at nitrogen dioxide, with it being possible to calculate nitrogen monoxide using the method already described.

Other materials suitable for use in gas-sensitive field effect transistors as gas-sensitive layers for the detection of nitrogen oxide, particularly nitrogen dioxide, are fine crystalline metal oxides operated at temperatures between 80° C. and 150° C. In particular these can be $SnO_2$, $WO_3$, $In_2O_3$, but salts from the carbonate systems such a barium carbonate or polymers such as polysiloxane are also conceivable.

Gas-sensitive layers of polysiloxanes can also be used for the detection of ethanol. Moisture is advantageously detected using gas-sensitive layers of polyamide or polypyrrolidone.

Phthalocyanines are particularly suitable for $\Delta\Phi$ measurements for detection of $NO_2$ gases with central atoms such as copper or lead, but also the compounds with tin, nickel, cobalt or zinc as the central atom. Phthalocyanine compounds and their derivates, that have no central atom, are particularly sensitive to $NO_2$; instead the free binding sites in the porphine ring are saturated by hydrogen atoms, such as in the case of heliogen blue G and a phthalocyanine with phenylether side chains. At sensor temperatures between room temperature and 120° C., $NO_2$ sensitivities down to the lower ppb range can be verified.

For verification of $NO_2$ in the lower ppb range, porphyrines and metalloporphyrines are suitable in addition to the phthalocyanine pigments. These include the metal-free porphyrines such as protoporphyrine IX sodium salt or metal-containing porphyrines such as cobalt protoporphyrines IX. To improve the response times of the sensors, the sensor layers are used at temperatures from room temperature up to 75° C.

An advantage of these investigated materials is that, compared with the phthalocyanines, at relatively low temperatures they have very small response times and a high $NO_2$ sensitivity. Thus, the sensors can also be operated at lower heater voltage, thus significantly reducing the power requirements of the sensor.

BRIEF DESCRIPTION OF THE DRAWINGS

The present invention will become more fully understood from the detailed description of preferred embodiments given hereinbelow and the accompanying drawings, which are given by way of illustration only and thus are not limitative of the present invention, and wherein.

DETAILED DESCRIPTION OF THE PREFERRED EMBODIMENTS

To determine the nitrogen oxide in exhaled air for the detection of asthma, it must be guaranteed that only the exhaled bronchial air is detected. Because air exhaled through the nose has a nitrogen oxide concentration increased by a factor of 1000, the volume of exhaled air to be measured must be precisely defined. This can be achieved by exhaling against a resistance, for example through a valve that opens only at increased air pressure, so that the soft pallet automatically closes and the breath is exhaled only through the mouth and not through the nose.

To verify nitrogen monoxide in the exhaled air it is necessary to preclude interference due to nitrogen oxide from the ambient air. To do this, the volumetric flow of the exhaled air is divided. One part of the exhaled air containing nitrogen is used directly for determining the residual concentration of $NO_2$. The second part is oxidized to nitrogen dioxide by way of a converter (oxidation catalyzer) and the nitrogen dioxide concentration is then measured. The actual nitrogen monoxide content of the exhaled air can be precisely determined from the difference between the concentrations of nitrogen dioxide.

The main advantages of the overall system are that a non-invasive method of measurement is used. The measurements are repeatable a large number of times and can thus also be used particularly to monitor the progress of therapy, to diagnose asthma in children, for the early detection of asthma or for preventive medicinal measures. The system with a gas sensor unit presented here is an exhaled gas sensor that is smaller to manufacture and more cost-effect to use and is therefore also suitable for use outside clinics and doctors' practices.

Figure 6:
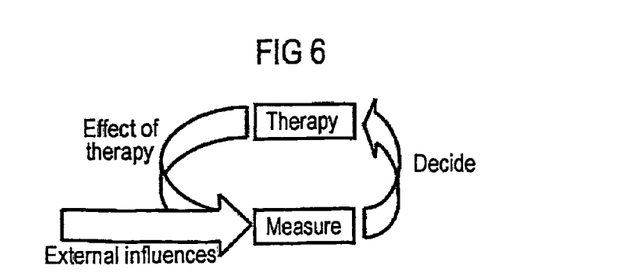
FIG. 6 shows the possibilities of converting a nitrogen monoxide measurement for diagnosis, planning therapy and monitoring progress of asthma sufferers.

FIG. 6 shows the chain of actions for illustration of an application scenario. Using asthma as an example, it can be stated that measurements of nitrogen monoxide concentrations as a key to the diagnosis of the planning of therapy and monitoring progress make a substantial contribution to the decision making. Further advantages of the arrangement in accordance with the invention lie in the elimination of cross-sensitivities or interference to measurements due to nitrogen oxide gases from the ambient air when determining the concentration of nitrogen monoxide.

Figure 3:
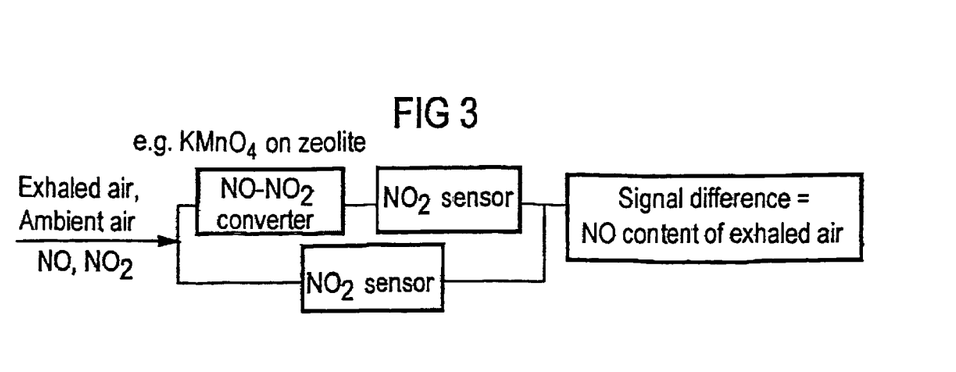
FIG. 3 shows the construction of a sensor system for determining the concentration of nitrogen monoxide in the exhaled air with the correction of cross-sensitivities, for example from the ambient air.

Because of the occurrence of nitrous oxides in the ambient air in concentration ranges relevant to the verification of an asthma illness, the disturbance effects from the ambient air must be eliminated. To do this, the nitrogen dioxide concentration already present in the exhaled air or that may enter the exhaled air due to sampling errors, must be directly determined by means of nitrogen dioxide gas sensors. In parallel with this, the nitrogen monoxide content in the exhaled air is quantitatively converted to nitrogen dioxide by means of a converter and quantified by a second nitrogen dioxide sensor. The differential signal of these two measurements then provides the amount of nitrogen monoxide in the exhaled air and verification for the assessment of the asthma illness. The described method is schematically shown in FIG. 3.

Figure 4:
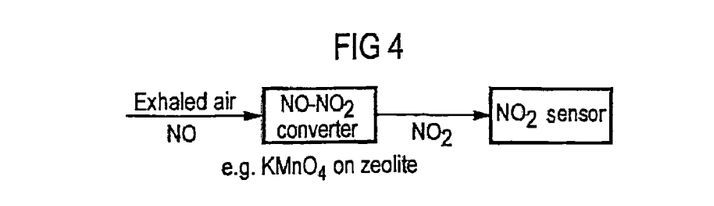
FIG. 4 shows the principle of conversion of nitrogen monoxide to nitrogen dioxide.

FIG. 4 shows a schematic for the conversion of nitrogen monoxide to nitrogen dioxide. To be able to determine the concentration of nitrogen monoxide in the exhaled air, the nitrogen monoxide content is quantitatively converted to nitrogen dioxide and the concentration is determined by way of a nitrogen dioxide sensor. For conversion of the measured gas, an oxidation agent such as permanganate salts or perchlorate salts is used, and is usually applied to a catalyst support such as zeolite, alumina or silica gel. This catalyst is placed in the gas flow of the exhaled gas so that the nitrogen monoxide contained in the exhaled air is quantitatively converted to nitrogen dioxide. This $NO_2$ gas is detected by means of highly-sensitive $NO_2$ gas sensors. The $NO_2$ content of the gas corresponds to the NO content of the exhaled air.

The elimination of the cross-sensitivities is accompanied by an improvement in the measuring accuracy. The sensor system for verification of an asthma illness is fitted with at least three sensors. The target gas nitrogen oxide, the humidity and ethanol are detected. An analytical circuit and the transmission of the data in a telemedical network result in particular advantages with regard to the detection and treatment of asthma.

Figure 5:
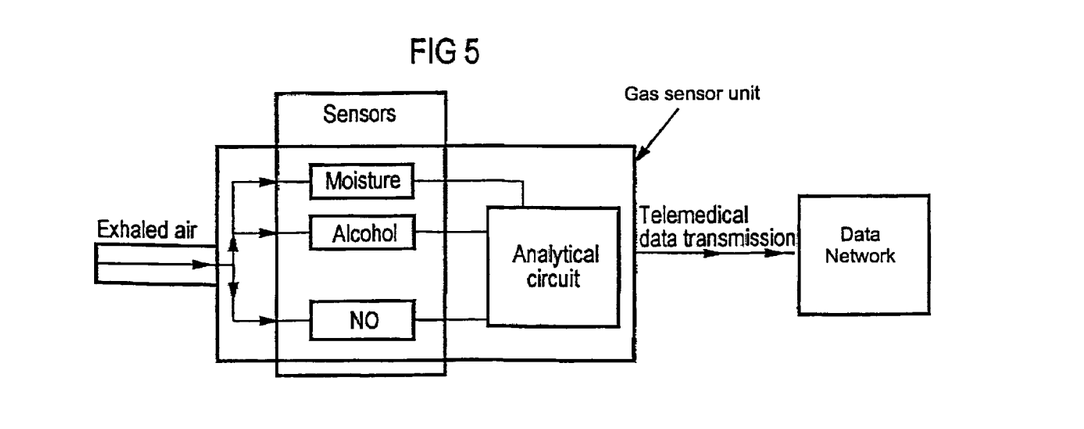
FIG. 5 shows a complete sensor system for determining the concentration of nitrogen monoxide in exhaled air.

The determination of the concentration of moisture and the direct signal correction with the NO sensor signal is necessary to eliminate the cross-sensitivity of the NO sensor layer to moisture. The determination of the alcohol concentration in the exhaled air is necessary to assess the quality of the NO measurement, because alcohol in the exhaled air can occur up to a level of 1500 ppm and can lead to falsification of the NO detection in the lower ppb range. FIG. 5 shows an example of a sensor system for determining the NO concentration in exhaled air. In this case, the exhaled air is not passed through a series of different sensors but is instead divided into different volumetric flows and supplied to corresponding, different sensors. Various volumetric flow measurements are necessary for this, in order to be able to calculate back to the part gas content in the exhaled air. Each step for NO detection in FIG. 5 contains corresponding functional units for conversion to $NO_2$ and its detection. Furthermore, by means of a further bypass contained in this NO stage, the basic concentration of $NO_2$ contained in the exhaled air, as shown in FIG. 3, can be determined.

A linking of the output signals of the system described by an embodiment of the invention enables asthma monitoring, with the nitrogen monoxide detection in the exhaled air being used as an essential part. The associated advantages are a simple location-independent operation and the ability to carry out regular reproducible measurements. The continual progress data obtained in this way provides information on factors that trigger an attack or on systematic incorrect behavior by patients. Because a change in the condition of the illness is signaled early in the NO values of the exhaled air, communicating the data quickly to the doctor providing the treatment enables medication to be adapted in good time, thus leading to a minimization of the amount of medication.

Figure 1:
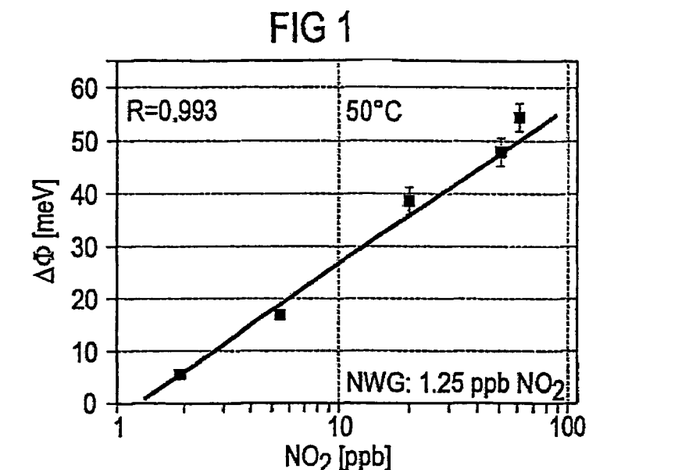
FIG. 1 shows an $NO_2$ characteristic curve of a sensor with a gas-sensitive layer of copper phthalocyanine.
Figure 2:
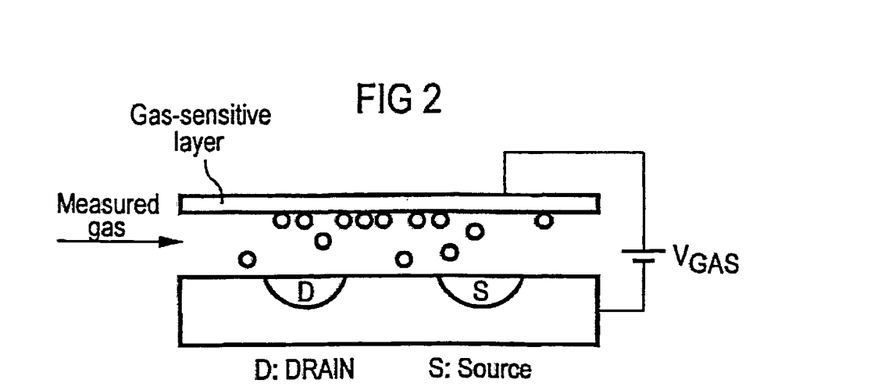
FIG. 2 shows a gas sensor using the principle of work function measurement as a suspended-gate FET.

FIG. 1 shows a change in the work function relative to the nitrogen dioxide content with a gas-sensitive layer of copper-phthalocyanine. FIG. 2 shows the concept of a gas-sensitive field effect transistor fitted with a gas-sensitive layer applied to a gate electrode spaced apart from the channel area. The signal at the gas-sensitive layer is read using the principle of work function measurement or according to the work function change.

Figure 7:
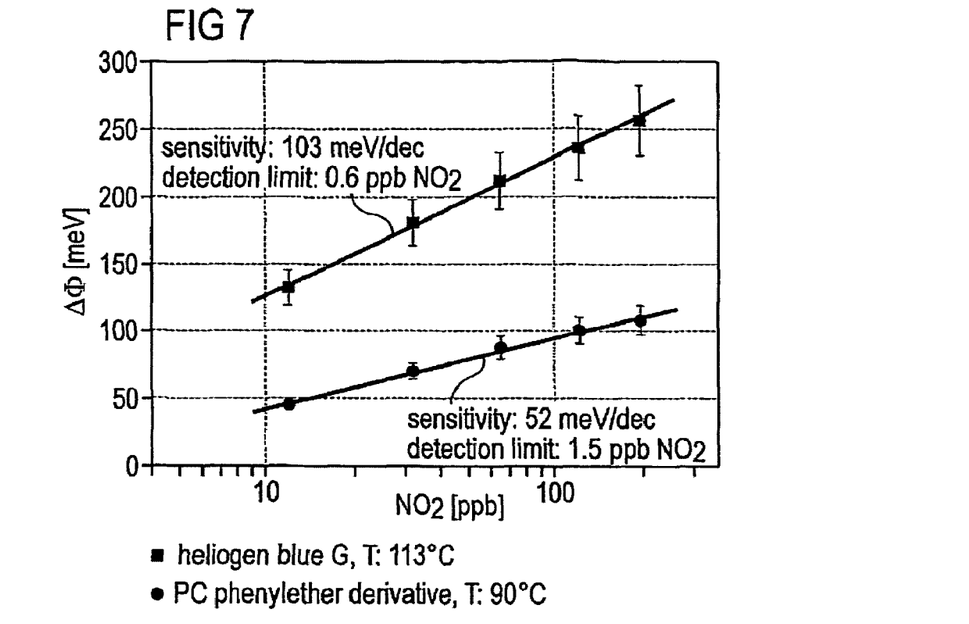
FIG. 7 shows a diagram with an $NO_2$ characteristic curve of heliogen blue G and of a phenylether derivate of an H2 phthalocyanine.
Figure 8:
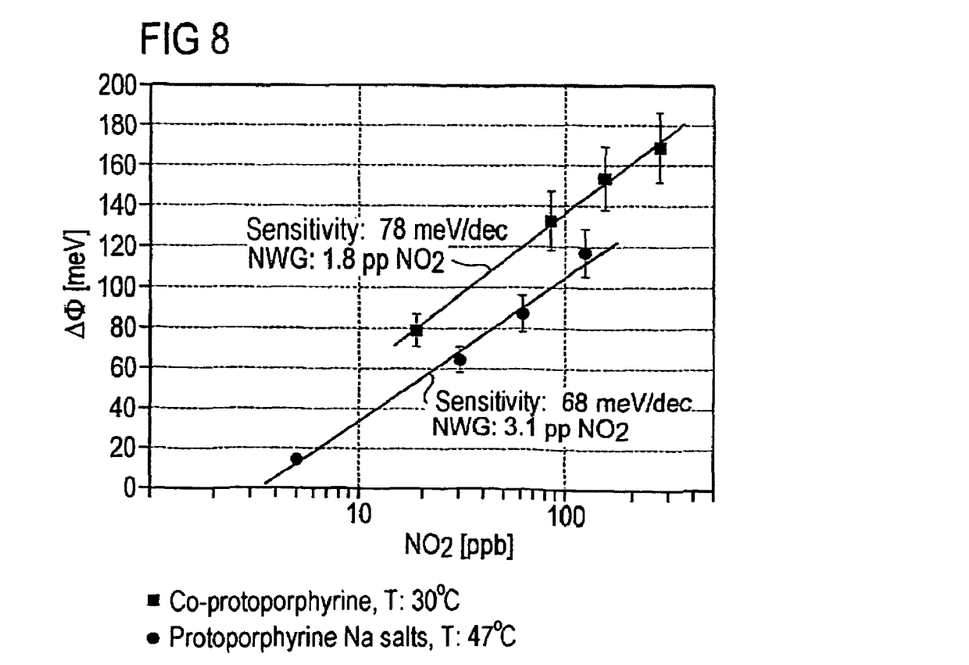
FIG. 8 shows a diagram with an $NO_2$ characteristic curve of co-protoporphyrine and one from metal-free protoporphyrine Na-salt.

FIGS. 7 and 8 show examples of certain NO sensors with specifically-chosen NO sensitive substances as a gas-sensitive layer in the sensor.

The advantages of the embodiments of the invention are revealed in particular in the application.

The determination of NO in exhaled gases is a non-invasive method of measurement that is particularly suitable for repeated applications, such as monitoring the progress of therapy, the diagnosis of asthma in children, the early detection of asthma or for preventive medical measures.

False measurements due to changes in temperatures at sensors or the presence of moisture can be corrected.

Interference due to high concentration of ethanol can be detected and corrected. The gas sensor system can be used for any number of repeatable measurements of the exhaled air.

The presented gas sensor is used for the manufacture of smaller and more cost-effective respiratory gas sensors and is therefore also suitable for use outside clinics and doctors' practices.

Figure 9:
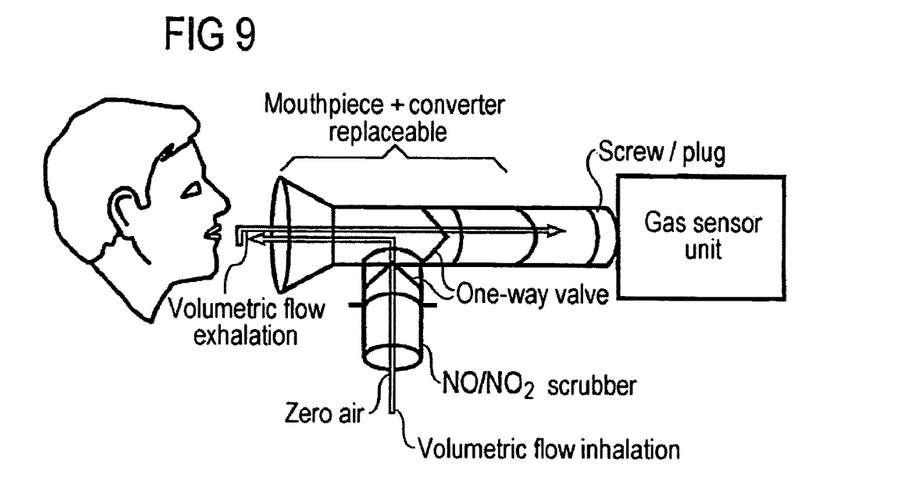
FIG. 9 shows the construction of a sampling system for use in an asthma sensor.

Construction of a measuring system for determining NO in exhaled air: The measuring system includes a sampling system and a gas sensor system. The sampling system, as shown in FIG. 9 includes a mouthpiece of biocompatible material, the $NO/NO_2$ converter for oxidation and a $NO/NO_2$ scrubber for elimination of $NO/NO_2$ from the measured gas. This sampling system can be flexibly connected to the gas sensor system, for example using threaded unions or plugs and can be renewed after one or more uses.

With aid of the sampling system, zero air, i.e. air that is free of NO and $NO_2$, is inhaled before the measurement by way of an $NO/NO_2$ scrubber. The $NO/NO_2$ scrubber includes a filter combination of active carbon and aluminum oxide or zeolite, or silica gel or a combination of these materials. This $NO/NO_2$ scrubber is fitted with a one-way valve so that inhalation is possible only through the $NO/NO_2$ scrubber and not through the converter column. This arrangement prevents NO or $NO_2$ gas, present in the ambient air in substantially higher concentrations than in the lungs, being inhaled into the lungs and thus increasing the levels in the exhaled air.

The exhaled air is blown through a second one-way valve to the $NO/NO_2$ converter and not through the $NO/NO_2$ scrubber. The converter includes potassium permanganate immobilized on silica gel.

The purpose of the converter is to:

convert the NO gas to $NO_2$ gas at room temperature and reduce the moisture in the exhaled gas.

Advantages of embodiments of the invention lie particularly in the application:

Air free of NO and $NO_2$ is inhaled, which indicates that the measurement is free of interference due to ambient air.

Dew formation on the sensor is avoided because silica gel absorbs part of the moisture in the breath.

There is no heater for the converter because oxidation of NO gas to $NO_2$ gas takes place at room temperature.

The replacement of system parts to be renewed, such as a mouthpiece that has to be renewed for reasons of hygiene or a converter that becomes used up and has to be replaced, is flexible and fast.

Figure 10:
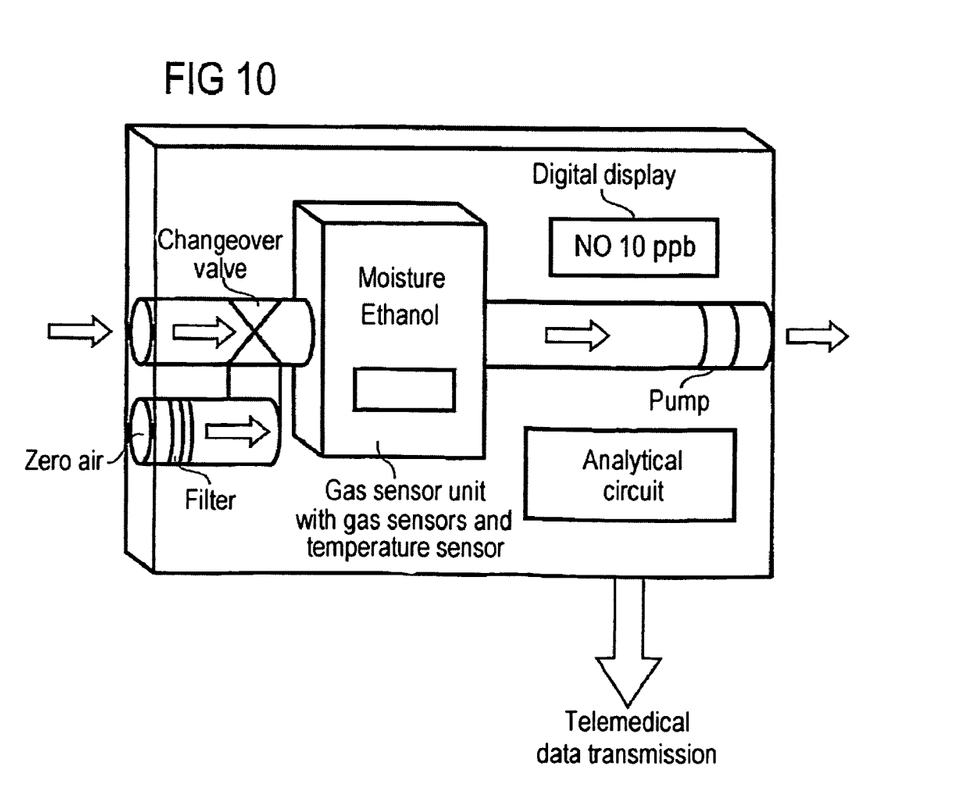
FIG. 10 shows a further example of a sensor system for determining the NO concentration in exhaled air.

The gas sensor measuring system corresponding to FIG. 10 includes a supply for the nitrogen dioxide-containing respiratory gas that is blown into the gas sensor unit through a changeover valve. In the gas sensor unit there are at least three gas sensors and three reference sensors for determining the $NO_2$ content, the moisture and the ethanol content in the exhaled air. Furthermore, it contains a temperature sensor for determining the gas temperature. Each sensor has a temperature regulator to set the temperature of the gas sensors. The gas sensor unit is followed by a gas outlet with a micropump. In addition to the gas inlet for the nitrogen dioxide-containing gas of the respiratory air, there is also a second gas inlet fitted with a filter system (active carbon+aluminum oxide/zeolite/silica gel combination). This filter system produces zero air and, after the gas has been measured, clears the measuring chamber/gas sensor unit and supply channels of $NO_2$ gas and other interfering gases and regenerates the gas sensors. With the aid of the micropump at the gas outlet and the changeover valve before the measuring chamber, the zero air, air free of $NO/NO_2$, is drawn in and the complete sensor system is regenerated and restored to the measuring mode.

The gas sensor system is also fitted with an analytical circuit to read the signals from the gas sensors and reference sensors, perform moisture correction, calculate the gas concentration and determine the NO concentration. The NO content is displayed on a digital display on the measuring system and is available for telemedical data transmission.

FIG. 9 particularly shows the improvement in the measuring arrangement by installing the converting column and arranging a zero air supply at the mouthpiece.

Exemplary embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

The invention claimed is:

1. Device for quantitative measurement of nitrogen monoxide in exhaled air, comprising:
   a gas sensor unit including
      at least one gas sensor based on a principle of work function measurement, the at least one gas sensor including a first-type gas-sensitive layer containing a porphine pigment,
      an oxidation catalyst for oxidation of nitrogen monoxide to nitrogen dioxide, and
      at least one further sensor for the detection of at least one of moisture and ethanol for elimination of cross-sensitivities,
   wherein the device is configured to measure the nitrogen monoxide, in the exhaled air of an individual, using the gas sensor unit.

2. Device according to claim 1, further comprising a field effect transistor including the first-type gas-sensitive layer, the field effect transistor being adapted to read the work function and the first-type gas-sensitive layer being in the form of a porous material deposited on a channel area of the field effect transistor.

3. Device according to claim 1, wherein the first-type gas-sensitive layer detects nitrogen oxide, the porphine pigment being a gas-sensitive material.

4. Device according to claim 3, wherein the porphine pigment is at least one of a phthalocyanine, a derivate of a phthalocyanine with the central atom being at least one of copper, lead, tin, nickel, cobalt, or zinc, and a phthalocyanine without a central atom whose free binding sites in the porphine ring are saturated by hydrogen atoms.

5. Device according to claim 4, wherein the phthalocyanine without the central atom is at least one of heliogen blue G and a phthalocyanine with phenylether side chains.

6. Device according to claim 1, wherein the device for determining the nitrogen monoxide in exhaled air is mobile.

7. Device according to claim 1, further comprising:
   a gas flow device for the supply of the volumetric flow of at least one of nitrogen dioxide and nitrogen dioxide and at least one component of at least one of moisture, ethanol and temperature.

8. Device according to claim 7, wherein the volumetric flow of the exhaled air is divided in the gas flow device into a part volumetric flow via the oxidation catalyst for oxidation of nitrogen monoxide to nitrogen dioxide and then to the gas sensor unit for measurement of the nitrogen dioxide concentration, and into a further part volumetric flow supplied directly to a further nitrogen dioxide gas sensor for determining the nitrogen dioxide concentration, wherein the nitrogen monoxide concentration of the exhaled air is calculatable by using the individual nitrogen dioxide concentrations.

9. Device according to claim 7, wherein the complete volumetric flow of the exhaled air in the gas flow device is supplied through the oxidation catalyst for oxidation of nitrogen monoxide to nitrogen dioxide and then to a gas sensor unit for measurement of the nitrogen dioxide concentration, wherein the nitrogen monoxide concentration of the exhaled air is calculatable by using the nitrogen dioxide concentration.

10. Device according to claim 8, wherein at least one substance from the group of at least one of permanganate salts and perchlorate salts is applied to a support including at least one of zeolite, aluminum oxide and silica gel as a material for the oxidation catalyst.

11. Device according to claim 1, wherein sensor signals processed in an analytical circuit are supplied to a data network.

12. Device according to claim 2, wherein the first-type gas-sensitive layer detects nitrogen oxide, the porphine pigment being a gas-sensitive material.

13. Device according to claim 12, wherein the porphine pigment is at least one of a phthalocyanine, a derivate of a phthalocyanine with the central atom being at least one of copper, lead, tin, nickel, cobalt, or zinc, and a phthalocyanine without a central atom whose free binding sites in the porphine ring are saturated by hydrogen atoms.

14. Device according to claim 13, wherein the phthalocyanine without the central atom is at least one of heliogen blue G and a phthalocyanine with phenylether side chains.

15. Device according to claim 9, wherein at least one substance from the group of at least one of permanganate salts and perchlorate salts is applied to a support including at least one of zeolite, aluminum oxide and silica gel as the material for an oxidation catalyst.

16. Device according to claim 1, wherein the at least one gas sensor includes:
a hybrid field effect transistor including the first-type gas-sensitive layer, the first-type gas-sensitive layer being represented by a gate electrode spaced apart from a channel area used to read the work function.

17. Device according to claim 16, wherein the hybrid field effect transistor is of a hybrid flip-chip construction.

18. Device according to claim 16, wherein the at least one further sensor includes at least one second-type gas-sensitive layer formed of a material that includes at least one of polyamides and polypyrrolidones for the detection of moisture or includes polysiloxanes for the detection of ethanol.

19. Device according to claim 16, wherein
the hybrid field effect transistor includes a second-type gas-sensitive layer in the form of porous material deposited on the channel area, wherein the hybrid field effect transistor is adapted to read the work function.

20. Device according to claim 16, wherein the first-type gas-sensitive layer detects nitrogen oxide, the porphine pigment being a gas-sensitive material.

21. Device according to claim 20, wherein the porphine pigment is at least one of a phthalocyanine, a derivate of a phthalocyanine with the central atom being at least one of copper, lead, tin, nickel, cobalt, or zinc, and a phthalocyanine without a central atom whose free binding sites in the porphine ring are saturated by hydrogen atoms.

22. Device according to claim 21, wherein the phthalocyanine without a central atom is at least one of heliogen blue G and a phthalocyanine with phenylether side chains.

23. Device according to claim 1, further comprising:
a hybrid field effect transistor including a second-type gas-sensitive layer represented by a gate electrode spaced apart from a channel area used to read the work function.

24. Device according to claim 23, wherein the hybrid field effect transistor is of a hybrid flip-chip construction.

25. Device according to claim 23, wherein the at least one further sensor includes at least one third-type gas-sensitive layer formed of a material that includes at least one of polyamides and polypyrrolidones for the detection of moisture or includes polysiloxanes for the detection of ethanol.

26. Device according to claim 23, further comprising:
a field effect transistor including the first-type gas-sensitive layer, the field effect transistor being adapted to read the work function and the first-type gas-sensitive layer being in the form of porous material deposited on the channel area.

27. Device according to claim 23, wherein the at least one first-type gas-sensitive layer detects nitrogen oxide, the porphine pigment being a gas-sensitive material.

28. Device according to claim 27, wherein the porphine pigment is at least one of a phthalocyanine, a derivate of a phthalocyanine with the central atom being at least one of copper, lead, tin, nickel, cobalt, or zinc, and a phthalocyanine without a central atom whose free binding sites in the porphine ring are saturated by hydrogen atoms.

29. Device according to claim 28, wherein the phthalocyanine without a central atom is at least one of heliogen blue G and a phthalocyanine with phenylether side chains.

30. Device according to claim 2, wherein the at least one further sensor includes a second-type gas-sensitive layer, wherein the second-type gas-sensitive layer is formed of a material that detects moisture and includes at least one of polyamides and polypyrrolidones and includes polysiloxanes for the detection of ethanol.

31. Device according to claim 2, wherein the at least one gas sensor includes the field effect transistor, and the field effect transistor has a hybrid flip-chip construction.

* * * * *